United States Patent
Lang (10) Patent No.: US 9,956,064 B2
(45) Date of Patent: May 1, 2018

(54) METHOD AND DEVICE FOR THE DETERMINATION OF THE CENTRIC POSITION OF A HUMAN SET OF TEETH

(71) Applicant: KALTENBACH & VOIGT GMBH, Biberach (DE)

(72) Inventor: Hans-Walter Lang, Leutkirch (DE)

(73) Assignee: KALTENBACH & VOIGT GMBH, Biberach (DE)

(*) Notice: Subject to any disclaimer, the term of this patent is extended or adjusted under 35 U.S.C. 154(b) by 191 days.

(21) Appl. No.: 14/446,841

(22) Filed: Jul. 30, 2014

(65) Prior Publication Data

US 2015/0030997 A1  Jan. 29, 2015

Related U.S. Application Data

(63) Continuation of application No. 12/063,977, filed as application No. PCT/EP2006/008129 on Aug. 17, 2006, now Pat. No. 8,827,933.

(30) Foreign Application Priority Data

Aug. 17, 2005 (DE) .......... 10 2005 038 898

(51) Int. Cl.
*A61B 5/103* (2006.01)
*A61B 5/117* (2016.01)
(Continued)

(52) U.S. Cl.
CPC ............ *A61C 19/045* (2013.01); *A61C 11/00* (2013.01); *A61C 11/005* (2013.01); *A61C 19/05* (2013.01);
(Continued)

(58) Field of Classification Search
CPC ....... A61C 7/002; A61C 11/00; A61C 11/005; A61C 19/045; A61C 19/05; A61C 19/052; A61B 5/4547
See application file for complete search history.

(56) References Cited

U.S. PATENT DOCUMENTS 4,234,306 A   11/1980 Hamada et al.
4,354,836 A   10/1982 Santoni
(Continued)

FOREIGN PATENT DOCUMENTS

BE   1003824 A6   6/1992
DE   19956876 A1  5/2001
(Continued)

OTHER PUBLICATIONS

Fukui et al., "Correlation Between Facial Morphology, Mouth Opening Ability, and Condylar Movement During Opening-Closing Jaw Movements in Femail Adults with Normal Occlusion," *European Journal of Orhodontics*, 24:327-336 (2002).
(Continued)

*Primary Examiner* — Devin Henson
(74) *Attorney, Agent, or Firm* — Marshall, Gerstein & Borun LLP (57) ABSTRACT

The invention concerns methods and a device for the determination of the centric position of a human set of teeth with improved precision. This is needed for the adjustment of an articulator in the production of dentures. For this purpose a plurality of successive bite movements or displacement movements of the lower jaw are recorded in form of electronic signal data and evaluated for the determination of the centric position.

6 Claims, 5 Drawing Sheets

(51) Int. Cl.
  *A61C 19/045* (2006.01)
  *A61C 11/00* (2006.01)
  *A61C 19/05* (2006.01)
  *A61B 5/00* (2006.01)
  *A61C 7/00* (2006.01)

(52) U.S. Cl.
  CPC ............. *A61B 5/4547* (2013.01); *A61C 7/002* (2013.01); *A61C 19/052* (2013.01)

(56) References Cited

U.S. PATENT DOCUMENTS

| | | | |
|---|---|---|---|
| 4,673,352 A | 6/1987 | Hansen | |
| 4,788,987 A | 12/1988 | Nickel | |
| 4,836,778 A | 6/1989 | Baumrind et al. | |
| 5,533,519 A | 7/1996 | Radke et al. | |
| 2005/0075585 A1 | 4/2005 | Kim et al. | |
| 2005/0153257 A1 | 7/2005 | Durbin et al. | |
| 2005/0251066 A1 | 11/2005 | Mack | |

FOREIGN PATENT DOCUMENTS

| | | |
|---|---|---|
| DE | 202004004955 U1 | 6/2004 |
| WO | WO-99/15100 A1 | 4/1999 |

OTHER PUBLICATIONS

English-language translation of International Preliminary Report on Patentability for Application No. PCT/EP2006/008129, dated Mar. 4, 2008.
English-language translation of International Search Report and Written Opinion for Application No. PCT/EP2006/008129, dated Dec. 7, 2006.
Office Action for U.S. Appl. No. 12/063,977, dated Aug. 17, 2011.
Office Action for U.S. Appl. No. 12/063,977, dated Dec. 2, 2011.
Office Action for U.S. Appl. No. 12/063,977, dated Aug. 9, 2013.
Office Action for U.S. Appl. No. 12/063,977, dated Mar. 13, 2014.

METHOD AND DEVICE FOR THE DETERMINATION OF THE CENTRIC POSITION OF A HUMAN SET OF TEETH

RELATED APPLICATIONS

This application is a continuation of U.S. application Ser. No. 12/063,977, filed Jun. 19, 2008, the entirety of which is hereby incorporated by reference herein.

BACKGROUND OF THE INVENTION

Field of the Invention

The invention finds application in the dental field, in particular in the production of dentures.

Related Technology

The most common technique for the production of dentures is the following. The dentist takes imprints of the teeth of the upper jaw and the lower jaw of the patient. Plaster models of the upper jaw and the lower jaw are produced from the imprints. These are placed in an articulator which consists of two parts which are connected with each other by two joints and which simulate the human set of teeth. The two joints correspond to the human jaw joints. After putting the plaster models in place the joints must be adjusted patient specifically.

A known method for the determination of the centric position consists in that a plate-like plastically deformable register is inserted between the opened teeth of the patient and the patient is then caused to bite. Through this imprints of the teeth of the upper jaw and the lower jaw are formed in the register. After hardening, the register is placed between the plaster models of the upper and lower jaw emplaced in a registry. Then, the lower jaw is displaced relative to the upper jaw, by adjustment of the two joints of the articulator representing the jaw joints, for so long that the teeth of the plaster models of the upper and lower jaw engage into the imprints on the two sides of the register with fitting seating.

Another likewise known method consists in that in each case a plate is fastened, in the mouth of the patient, to the teeth of the upper jaw and the lower jaw by means of a plastically deformable mass. The two plates extend through the oral cavity. The plate fastened to the teeth of the lower jaw carries a supporting pin rising up in the middle. The plate fastened to the teeth of the upper jaw has a wax layer at its underside in which the supporting pin, upon impingement, produces an imprint. The imprint defines the centric position. The two plates are then removed from the mouth of the patient and put onto the teeth of the plaster models in the articulator. The joints of the articulator are then so displaced that the supporting pin again dips into the imprint of the wax layer at the underside of the upper plate. With that, the articulator is adjusted to the centric position. Thus, here, the centric position is a reference position fixed in the patient mouth and in employed in the articulator for adjustment.

A third known method for the determination of the centric position is a variation of the second method just described. Here, the patient is not only caused to bite once, but rather his lower jaw is to carry out a fore and back movement, as well as side movements to two sides. Thereby, a T-like trace arises in the wax layer of the upper plate, wherein the upper T-limb is upwardly arched. One calls this arching a Gothic arch. The intersection point of the two T-limbs is now selected as that point with which the support pin is lined up in the articulator for adjusting the centric position.

There is also known a device sold by Kalten & Voigt GmbH (Germany) under the trade name "Digma" or "ARCUS-Digma". This device is an aid for the setting of articulators. For this purpose, it carries out an electronic position analysis of the lower jaw. To measure the movements of the lower jaw with respect to the upper jaw in each case there is connected with the upper jaw and the lower jaw a carrier frame. The carrier frame connected to the upper jaw at the upper part of the head has four microphones; the carrier frame connected to the lower jaw has three ultrasound transmitters. The twelve paths between the three transmitters and the four microphones are evaluated with regard to their length changes upon movement of the lower jaw. Up to now, the device has not found any application for the determination of the centric position.

GENERAL DESCRIPTION OF THE INVENTION

The invention addresses the task of solving the problem described below. If a patient moves the lower jaw with respect to the upper jaw and the teeth meet each other, then this does not mean inevitably that the upper jaw always takes up the same position with respect to the lower jaw. The mentioned position rather differs in dependence upon the tension of the chewing muscles, upon signals issued by the teeth when they meet one another, upon of the pressure on the menisci in the jaw joints and upon various signals from the brain. The latter are influenced by whether the patient is tired or is under stress. The previous methods for the determination of the centric position are therefore inaccurate and this because the single bite or single movements is or are subject to random factors. The invention is based on the object of improving the precision of the method for the determination of the centric position.

Starting out from the second known method for the determination of the centric position a first solution in accordance with the invention utilizes a method wherein a plurality of biting movements are carried out, wherein the biting movements are detected using measurement technology and converted into electrical signal data, and wherein from the signal data of a plurality of end positions the centric position is determined.

The centric position can be determined for example by averaging of the signal data of the plurality of end positions in a coordinate plane.

In another embodiment of the invention, only the signal data items, in one coordinate plane, lying in a restricted hit field are evaluated.

Starting out from the third known method for the determination of the centric position of a human set of teeth, described above, in which the lower jaw is caused to carry out at least one movement with respect to the upper jaw and in which at least two movements are evaluated for the determination of the centric position, in a further method in accordance with the invention for solution of the problem the lower jaw in the bite end position is caused to carry out a plurality of first displacement movements running between the forward and the rearward end position as well as a plurality of second displacement movements running between the two lateral end positions, in that the first and second displacement movements are detected using measurement technology and transformed into electrical signal data, and in that the signal data is evaluated to the effect that the intersection point of the first and the second displacement movements is determined as centric position. The signal data of the first and the second displacement movement as well as the signal data of the determined centric position can be represented on a display as symbols, such as e.g. points. The representation can be effected in a coordinate plane, in which the coordinates are Cartesian coordinates.

A certain centric position need not necessarily be coupled with certain positions of the two jaw joints. Due to asymmetric biting by the patient a certain centric position can also correspond to different pairs of jaw joint positions. If one wishes to remove this uncertainty, further information must be available for the adjustment of the articulator. This is for example the case if the centric position is used to program (introduction of tooth imprints) a register. For this purpose, the patient—possibly with the guiding support of the dentist—moves his lower jaw of into the determined centric position, so that the teeth of upper and lower jaw produce imprints in a plastic register placed between them. The imprints contain the additional information about the jaw joint positions. The register then can be used, in accordance with the known method described first, in the articulator to adjust the joints thereof.

Alternatively to this it is possible, alongside or instead of the signal data for the one centric position, to determine the corresponding signal data for a mean position of the two jaw joints. If these data are available, the use of a register can be foregone. The mean position of the two jaw joints can then be used directly for adjustment of the two joints of the articulator, by either hand or by motorized means.

In one embodiment, the signal data of the bite end positions of all biting movements and the signal data of the determined centric position are represented on a display as symbols, such as points for example. The representation can be effected in a coordinate plane which allows the actual spacings of the bite end positions from the centric position to be recognized in corresponding measurement units. Preferably, Cartesian coordinates are used for this.

In another embodiment, the signal data of the jaw joint positions corresponding to the centric position are represented on a display as symbols, such as points for example, in each case in two coordinate planes, and in that the coordinate planes include an angle, preferably an angle of 90°. The one coordinate plane may represent for example that sectional plane through the patient head which runs on the one hand between above (cranial) and below (cardial) and on the other hand in front (ventral) and behind (dorsal), and in that the other coordinate plane represents that sectional plane through the patient head which on the one hand runs between in front (ventral) and behind (dorsal) and on the other hand between the body axis (medial) and the appropriate side (lateral). The coordinates may be represented in the manner of polar coordinates in the form of concentric rings. Thereby, the symbols for the jaw joint positions which correspond to the centric position, with freedom from pain of the jaw joints, can be displaced into the centre of the polar coordinates as a reference for all other possible jaw joint positions.

The device for carrying out one of the above-described methods for the determination of the centric position of a human set of teeth may have, like the known Digma device, carrier frames for sender and receiver elements, wherein in each case one carrier frame is connectable in a reproducible position with the lower jaw and the upper jaw of the patient in question and wherein the distances between the transmitter and receiver elements are measured and evaluated for obtaining signal data.

Thereby, it has proved that the precision provided with the four sender elements and three receiver elements of the known Dig ma device is insufficient to ensure the desired precision for the determination of the centric position. The device in accordance with the invention is therefore different from the known Digma device in that, among other things, more than three sender elements and more than four receiver elements are provided. Further relevant differences arise from the corresponding means with which the individual method steps are to be realized. These means arise from the method steps (e.g. means for the calculation of the mean value from the signal data etc.).

BRIEF DESCRIPTION OF THE DRAWING

The invention will be explained below with reference to the drawings.

DETAILED DESCRIPTION

Figure 1:
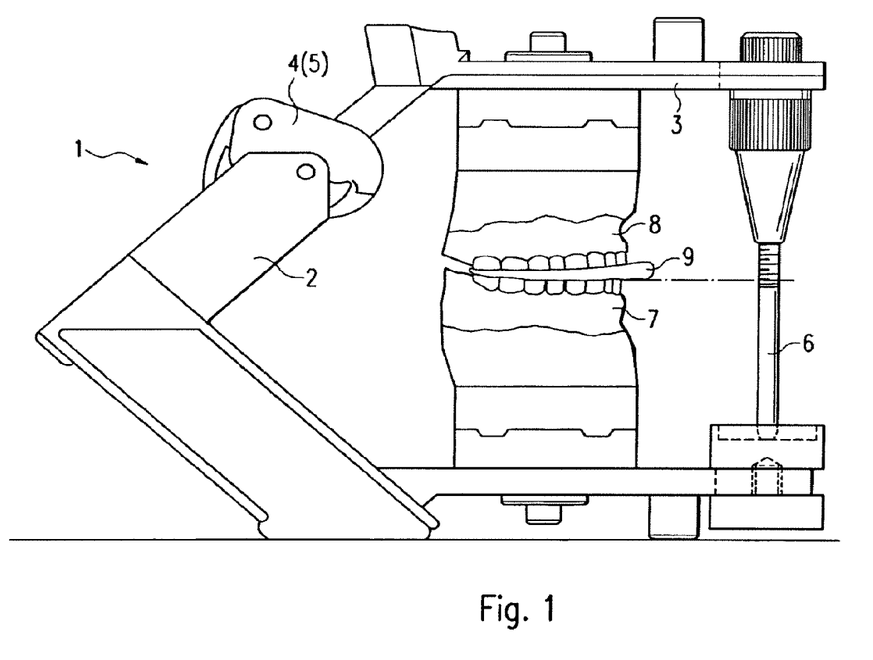
FIG. 1 shows an articulator with plaster models and register in place.

The articulator 1 shown in FIG. 1 is conventional and described e.g. in DE 42 11 020 C2. It includes two yokes 2, 3 which are connected with each other by joints 4, 5 of which only one is visible here. The joints 4, 5 are adjustable for setting the centric position. The spacing of the yokes is regulatable with a supporting pin 6. A plaster model 7 of the lower jaw of a patient is attached to the yoke 2. A plaster model 8 of the upper jaw of the patient is attached to the yoke 3. A register 9, of a curable, initially plastically deformable material, is located between the teeth of the two plaster models 7, 8.

For the making of the two plaster models 7, 8, at first the dentist must take imprints of the teeth of the upper jaw and the lower jaw. For this he uses shells adapted to the tooth row form, in which a plastically deformable mass is located, which the dentist presses onto the teeth. Liquid plaster is then cast into the mould provided in this way, which after hardening yields plaster models of the upper jaw and of the lower jaw of the patient. Then, with the conventional method for the determination of the centric position, the patient is caused by the dentist to move the lower jaw against the upper jaw in the form of a single biting movement, so that imprints of the teeth of the upper jaw and the lower jaw are formed in the register 9. The substrate 9 is then, after hardening, placed in the articulator between the teeth of the two plaster models 7, 8 as illustrated in FIG. 1. To ensure that the articulator simulates as far as possible the parameters of the set of teeth of the patient, now the joints 4, 5 of the articulator and the distance pin 6 are so adjusted that the teeth of the two plaster models 7, 8 engage into the imprints of the register 9 in form-fitting manner. When this adjustment is complete, the plaster model can be processed in a conventional manner for the production of dentures.

However, it has proved that the previous method of determination of the centric position is inaccurate because the single bite is affected by random factors, for example affected by the state of stress of the patient, by the sensitiveness of his teeth when meeting the counter-teeth, as well as by the condition of the menisci in the jaw joints.

Thus, to increase the precision in the determination of the centric position on the one hand there is used an electronic measurement procedure known in itself, with which previously the movement of the lower jaw with respect to the upper jaw has been determined in three dimensions. In other words with this method electronic signal data is produced and evaluated for representation of the movements of the lower jaw. Alongside the application of the known electronic measurement procedure, a statistical evaluation of a plurality of movements of the lower jaw with respect to the upper jaw is carried out.

Figure 2:
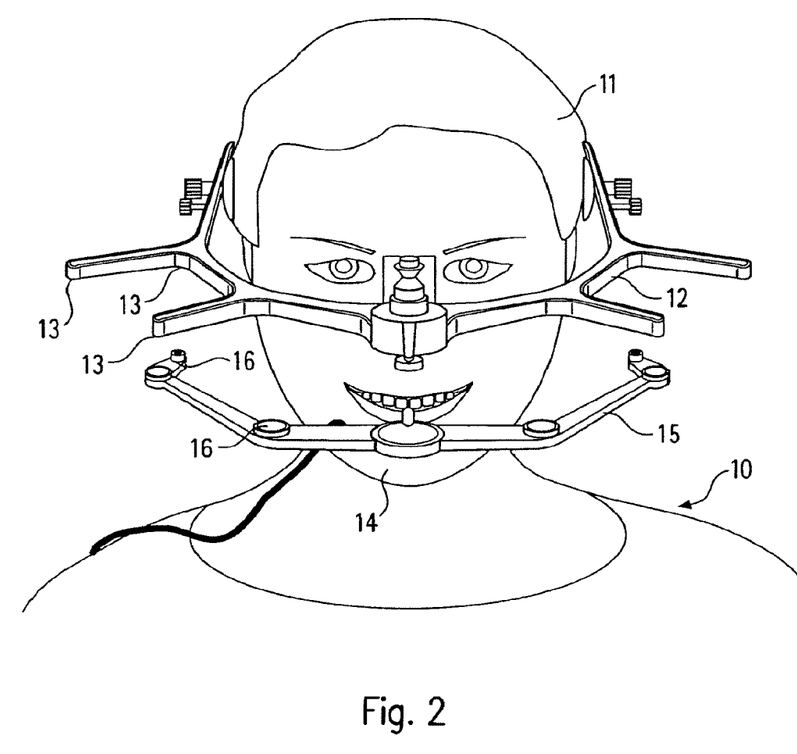
FIG. 2 shows the head of a patient with in-place carrier elements for the sender and sensor elements.

The new measuring arrangement for the determination of the centric position is shown in FIG. 2. On the upper part of the head 11 of a patient 10 there is attached a carrier frame 12 which has four arms. Each arm carries two downwardly directed ultrasound microphones as receiver elements. A further carrier frame 15 is connected with the lower jaw 14 of the patient 10. This is adhered by means of a bite fork on the teeth of the lower jaw with the use of a plastic mass. The frame 15 carries four upwardly directed ultrasound transmitters as sender elements.

In the case of the known Digma device one works with three sender elements and four receiver elements. This yields twelve measurement sections, length changes of which are evaluated upon movement of the lower jaw. It has proved, however, that the thus obtainable measuring precision is not sufficient to determine the centric position with the now desired precision. The precision is, however, achieved with the new device by the eight sender elements and four receiver elements provided, with which 32 measurement sections can be evaluated. It is, however, emphasized at this point that the number of the sender elements and the receiver elements has effect only with regard to the precision, but is not decisive for the fundamental function of the methods in accordance with the invention.

Figure 3:
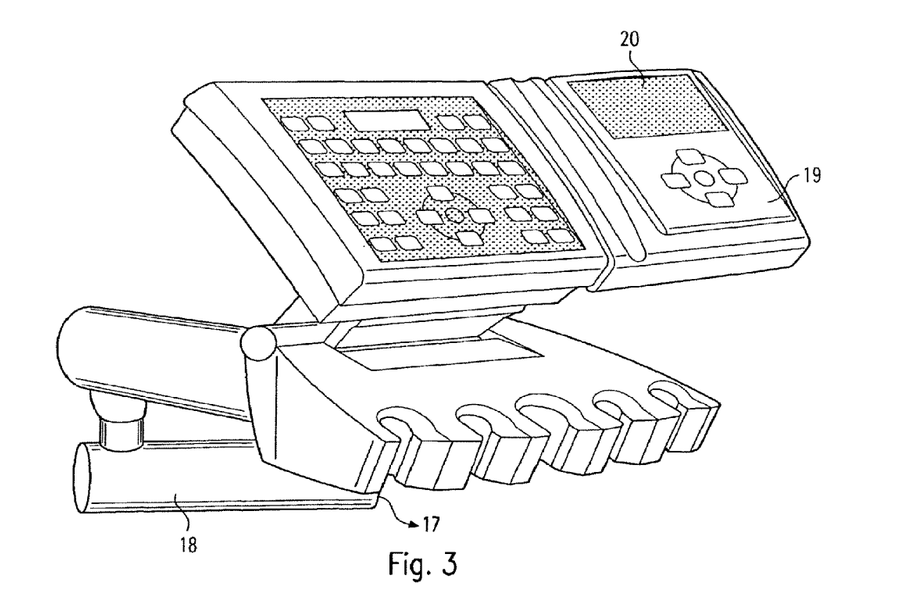
FIG. 3 shows a device for centric determination.

A new device 19 for carrying out the methods in accordance with the invention is shown in FIG. 3. It is docked on the arm 18 of a dental treatment unit 17 and has a display 20. The device 19 is connected via connection cable or in cableless manner with the sender elements 16 and the receiver elements 13 on the carrier frames 12 and 15 in FIG. 2. It measures the bite end positions of the lower jaw 14 in the form of signal data.

Figure 4:
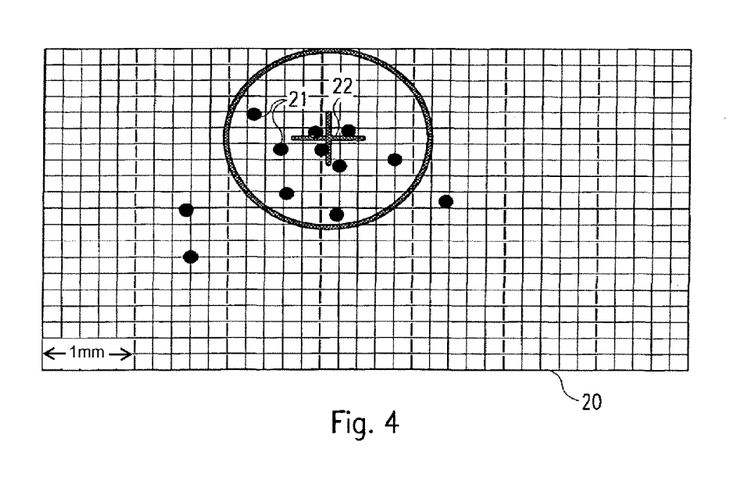
FIG. 4 shows a display with different hits for the selection of the centric position.

The bite end positions of a plurality of successive biting movements of the patient are illustrated on the display 20, illustrated in FIG. 4 to an enlarged scale, in the form of points 21. The display is covered with a grid of Cartesian coordinates. One recognizes that the bite end positions differ more or less from each other. The points 21 lying within a hit field indicated by a circle are evaluated for the determination of the centric position. One possibility for the evaluation is an averaging from the coordinates of all points 21 which lie in the hit field. The mean value is indicated by the cross 22 and illustrates the centric position. On the basis of knowledge of the centric position 22 the dentist can now, by guiding of the lower jaw, cause the patient to move the lower jaw in a new single biting movement into the bite end position indicated by the centric position and to program a register placed between the teeth. The thus programmed register 9 is then placed between the teeth of the two plaster models in the articulator 4 (FIG. 1). After that the joints 4, 5 of the articulator 4 are so positioned in known manner that the teeth of the plaster model 7, 8 engage into the corresponding imprints in the register 9 in form-fitting manner.

Figure 5:
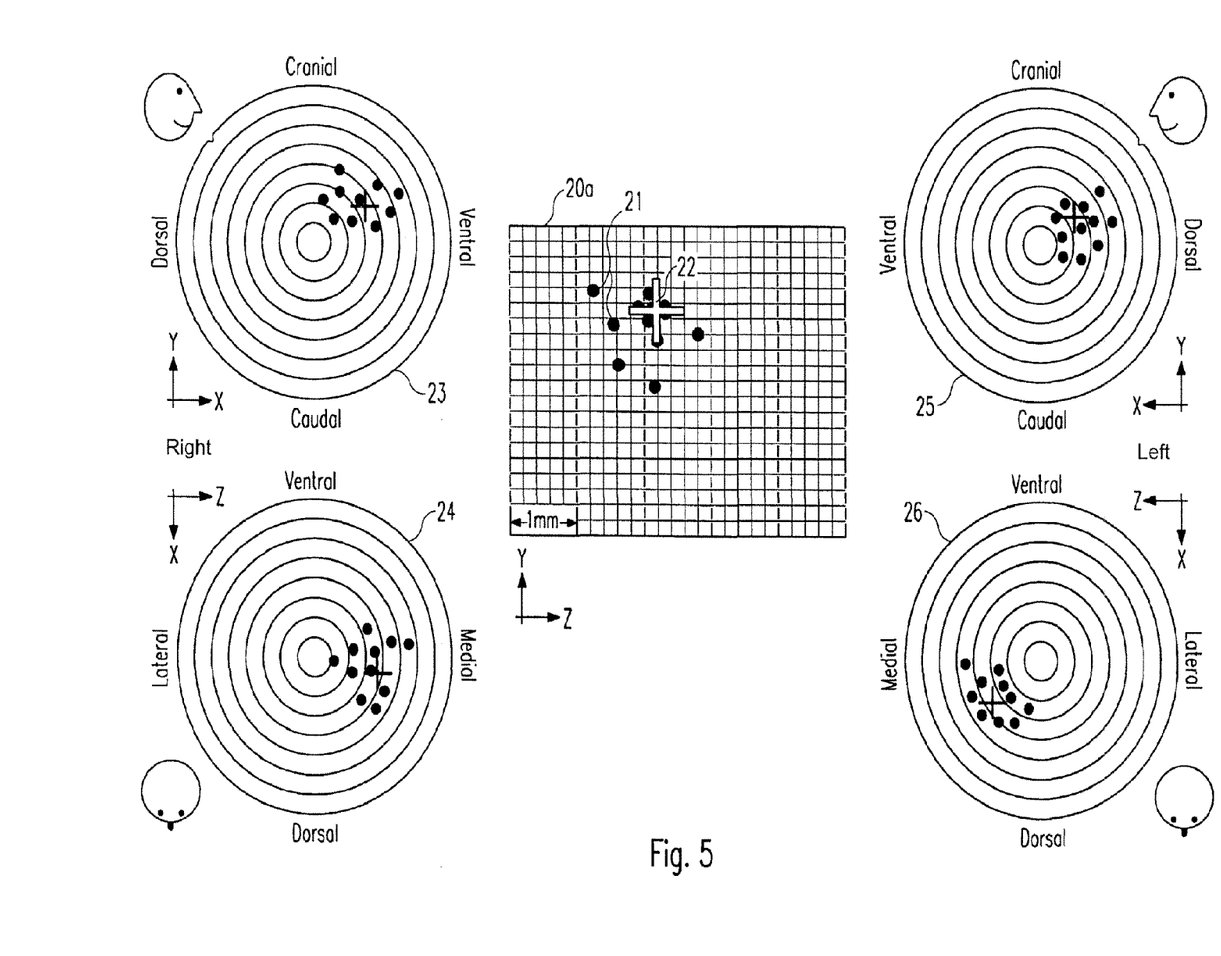
FIG. 5 shows a display as in FIG. 4 additionally with four polar coordinate planes for the indication of the tested jaw joint positions.

In addition or instead of the signal data of the determined centric position also the jaw joint positions of the patient can be determined. This is shown in FIG. 5. The screen 20 shows here a coordinate system 20a in reduced form, likewise with points corresponding to a plurality of different bite end positions and the centric position 22 determined therefrom. Besides the representation 20a, there are represented on the screen 20, respectively on the left and on the right, two polar coordinate planes 23, 24; 25, 26 which represent sections through the head of the patient. The sections are designated by medical terms (dorsal, caudal, ventral, cranial, lateral and medial) and by the stylized head symbols located beside the polar coordinate planes. The polar coordinate planes 23-26 have the form of concentric rings. The centric position 22 in the Cartesian coordinate plane 20a shown in the centric position 22 corresponds to the polar coordinate points in the four polar coordinate planes 23-26. The plurality of bite end positions yield also in the polar coordinate planes a corresponding number of points and through the evaluation of their positions a centric position in form of a cross.

Instead—as was explained in connection with FIG. 4—of now using the determined centric position to program a register, it is possible to directly use—i.e. without the intermediary of a register—the centric positions of the jaw joints set down in FIG. 5 in the polar coordinate planes, for adjustment of the joints of the articulator 1. For this there should be provided on the articulator a sender-sensor system which corresponds to that in FIG. 2. In this case the person carrying out the adjustment of the jaw joints can orientate himself on the display. As an alternative to this it is however also possible that the joints of the articulator are adjustable in motorized manner in three dimensions so that the adjustment of the joint positions of the articulator need not be effect by hand but is carried out automatically.

Figure 6:
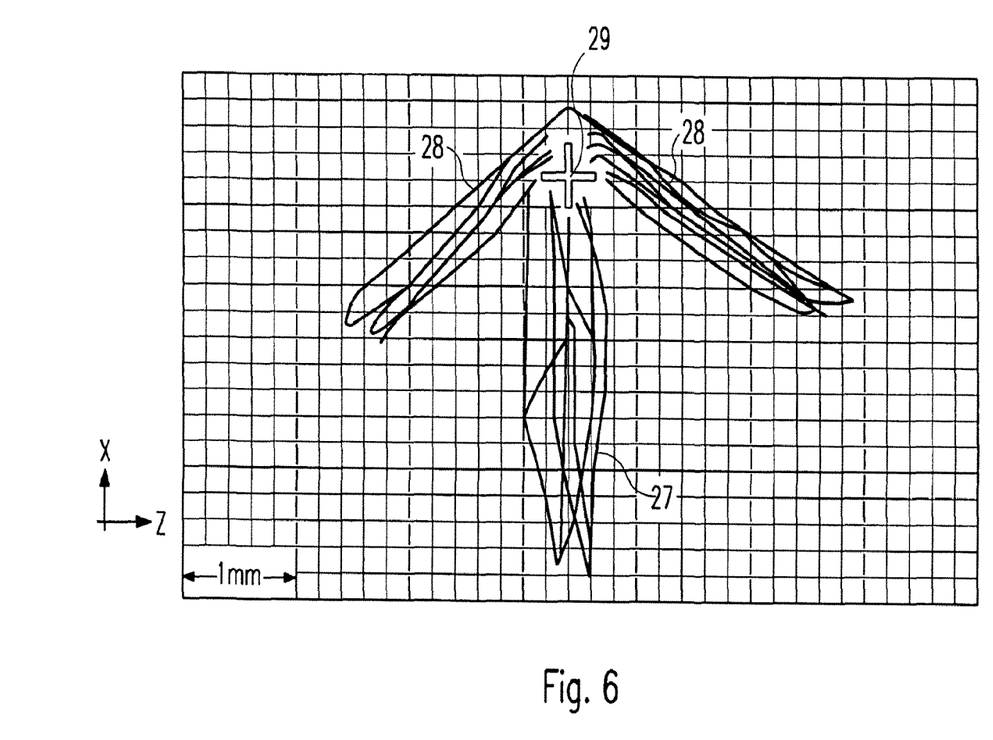
FIG. 6 shows a display as in FIG. 4 in the case of which, however, another method for centric determination was selected.

A third method for the determination of the centric position is shown in FIG. 6. Here the display 20 is again shown with a Cartesian coordinate system. The dentist causes the patient to move the lower jaw, with teeth lying on each other completely or largely, to the front and to the rear as well as to the two sides. In this way a T-like movement pattern of lines appears on the screen, wherein the lines 27 represent the forward and backward movement of the lower jaw and the lines 28 represent the side movements of the lower jaw. The upper limb of the T hangs down, i.e. is pointed or arched. The determination of the centric position is effected by the evaluation by all movement lines, for example by averaging, wherein the intersection point between the two T-limbs is determined as centric position 29 which is represented here again as a cross. In turn this centric position can be used for the programming of a register or, in connection with the polar coordinates shown in FIG. 5, used for direct adjustment of the articulator.

The invention claimed is:

1. Method for the determination of the centric position of a human set of teeth, comprising:
   carrying out a plurality of biting movements of a patient's lower jaw;
   detecting a plurality of bite end positions during the biting movements with measurement technology for each biting movement;
   converting the plurality of bite end positions into electrical signal data in the form of points having coordinates;
   determining a centric position from the signal data by averaging the coordinates of the plurality of bite end positions in a coordinate plane;
   illustrating the coordinates of the determined centric position on a display;

placing a register between the patient's upper and lower jaw;

guiding the patient's lower jaw into the centric position illustrated on the display by manipulating the patient's lower jaw until a measured position of the patient's lower jaw matches the illustrated determined centric position on the display; and programming the register by bringing the patient's lower jaw into contact with the register to imprint the register.

2. Method according to claim 1, wherein, for the determination of the centric position, only signal data items lying in the coordinate plane in a restricted hit field are evaluated.

3. Method according to claim 1, wherein the signal data of the plurality of bite end positions and the signal data of the determined centric position are represented on a display as symbols.

4. Method according to claim 3, wherein the symbols are represented on the display in a coordinate plane which allows actual spacings of the bite end positions from the centric position to be recognized in appropriate measurement units.

5. Method according to claim 4, wherein coordinates of the coordinate plane are Cartesian coordinates.

6. Method according to claim 1, further comprising:

placing the register between two plaster models in a dental articulator; and adjusting joints of the dental articulator so that teeth of the two plaster models engage the corresponding imprints on the register.

* * * * *